(12) United States Patent
Musselmann et al.

(10) Patent No.: US 7,834,153 B2
(45) Date of Patent: Nov. 16, 2010

(54) COMBINATION OF INSULIN AND ASCORBATE TO ENHANCE WOUND HEALING

(75) Inventors: Kurt Musselmann, Tampa, FL (US); John R. Hassell, Tampa, FL (US); Brad Kane, Lakeland, FL (US); Bridgette Alexandrou, Tampa, FL (US)

(73) Assignee: University of South Florida, Tampa, FL (US)

( * ) Notice: Subject to any disclaimer, the term of this patent is extended or adjusted under 35 U.S.C. 154(b) by 512 days.

(21) Appl. No.: 11/758,080

(22) Filed: Jun. 5, 2007

(65) Prior Publication Data

US 2007/0281882 A1 Dec. 6, 2007

Related U.S. Application Data

(60) Provisional application No. 60/803,944, filed on Jun. 5, 2006, provisional application No. 60/823,583, filed on Aug. 25, 2006.

(51) Int. Cl.
*A61K 36/39* (2006.01)
*A61K 8/65* (2006.01)

(52) U.S. Cl. .................................... 530/356; 424/78.06

(58) Field of Classification Search ........................ None
See application file for complete search history.

(56) References Cited

U.S. PATENT DOCUMENTS

| 6,187,743 | B1 | 2/2001 | Obi-Tabot |
| 6,359,007 | B1 | 3/2002 | Pearson |
| 2001/0006646 | A1 * | 7/2001 | Coyne ........................ 424/400 |
| 2003/0181386 | A1 | 9/2003 | Nishida et al. |
| 2004/0248871 | A1 | 12/2004 | Farjanel et al. |
| 2006/0045926 | A1 | 3/2006 | Nimni et al. |

FOREIGN PATENT DOCUMENTS

LT 4382 B * 3/1998

OTHER PUBLICATIONS

Koob, 1987, Biochem. J., 246, 589-598.*
Saika, Graefe's Arch Clin Exp Ophthamol., 1993, 231, 221-227.*
Zaras, 1998, LT 4382, 11 pages (Translation of original document).*
Whitson, S. W., Whitson, M. A., Bowers, Jr. D. E. and Falk, M. C. 2004. Factors Influencing Synthesis and Mineralization of Bone Matrix from Fetal Bovine Bone Cells Grown In Vitro. Journal of Bone and Mineral Research. vol. 7, No. 7. Alton, IL.
Qutob, S., Dixon, S. J., and Wilson, J. X. 1998. Insulin Stimulates Vitamen C Recycling and Ascorbate Accumulation in Osteoblastic Cells. Endocrinology. vol. 139. No. 1. United States.
Libby, P. And O'Brien, K. V. 1983. Culture of Quiescent Arterial Smooth Muscle Cells in a Defined Serum-Free Medium. J Cell Physiol. vol. 115, No. 2. United States.
Prehm, P., Dessau, W., and Timpl, R. 1982. Rates of Synthesis of Basement Membrane Proteins by Differentiating Teratocarcinoma Stem Cells and Their Modulation by Hormones. Connect Tissue Res. vol. 10, No. 3-4. England.
Guerriero, E., Chen, J., Sado, Y., Mohan, R. R., Wilson, S., Funderburgh, J. L., and Sundarraj, N. 2007. Loss of Alpha3(IV) Collagen Expression Associated with Corneal Keratocyte Activation. Investgative Ophthalmology & Visual Science. vol. 48, No. 2 United States.
Provenzano, P. P., Alejandro-Osorio, A., Grorud, K. W., Martinez, D. A., Vailas, A. C., Grindeland, R. E., Vanderby Jr., R. 2007. Systemic Administration of IGF-I Enhances Healing in Collagenous Extracellular Matrices: Evaluation of Loaded and Unloaded Ligaments. BMC Physiology vol. 7:2.
Saragas, S., Arffa, R., Rabin, B., Kronish, J., Miller, D., and Mayman, C. 1985. Reversal of Wound Strength Retardation by Addition of Insulin to Corticosteroid Therapy. Ann Ophthalmol 17(7):428-30.
Madibally, S. V., Solomon, V., Mitchell, R. N., Van De Water, L., Yarmush, M. L., and Toner, M. 2003. Influence of Insulin Therapy on Burn Wound Healing in Rats. Journal of Surgical Research vol. 109, pp. 92-100.
Brodovsky, S. C., Mccarty, C. A., Snibson, G., Loughnan, M., Sullivan, L., Daniell, M., and Taylor, H. R. 2000. Management of Alkali Burns an 11-Year Retrospective Review. Ophthalmology. vol. 107. pp. 1829-1835.
Ramirez, R. J., Wolf, S. E., Barrow, R. E., and Herndon, D. N. 1998. Growth Hormone Treatment in Pediatric Burns: A Safe Therapeutic Approach. Annals of Surgery vol. 228. No. 4, pp. 439-448.
Pierre, E. J., Barrow, R. E., Hawkins, H. K., Hal, K., Nguyen, T. T., Sakuri, Y., Desai, M., Wolfe, R. R., and Herndon, D. N. 1998. Effects of Insulin on Wound Healing. The Journal of Trauma, Injury, Infection and Critical Care. vol. 44(2), pp. 342-345.
Whitson, S. W., Whitson, M. A., Bowers, Jr D. E. And Falk, M. C. 2004. Factors Influencing Synthesis and Mineralization of Bone Matrix from Fetal Bovine Bone Cells Grown In Vitro. Journal of Bone and Mineral Research. vol. 7, No. 7. Alton, IL.
Qutob, S., Dixon, S. J., and Wilson, J. X. 1998. Insulin Stimulates Vitamen C Recycling and Ascorbate Accumulation in Osteoblastic Cells. Endocrinology. vol. 139. No. 1. United States.

(Continued)

*Primary Examiner*—Cecilia Tsang
*Assistant Examiner*—Satyanarayana R Gudibande
(74) *Attorney, Agent, or Firm*—Michele L. Lawson; Smith & Hopen, P.A.

(57) ABSTRACT

Provided is a method of stimulating collagen synthesis and proteoglycan (lumican and keratocan) accumulation. Collagenase isolated keratocytes were cultured with or without insulin with or without ascorbate. Insulin stimulates the synthesis of collagen but does not affect the accumulation of lumican and keratocan. Insulin plus ascorbate, however, stimulates the synthesis of collagen and increased the accumulation of these proteoglycans. The accumulation of PGDS, a KSPG that does not interact with collagen, is not affected by ascorbate. Only the collagen made in the presence of ascorbate was pepsin resistant. EDB overrode the effects of ascorbate on pepsin resistance and proteoglycan accumulation.

1 Claim, 7 Drawing Sheets

OTHER PUBLICATIONS

Libby, P. and O'Brien, K. V. 1983. Culture of Quiescent Arterial Smooth Muscle Cells in a Defined Serum-Free Medium. J Cell Physiol. vol. 115, No. 2. United States.

Prehm, P., Dessau, W., and Timpl, R. 1982. Rates of Synthesis of Basement Membrane Proteins by Differentiating Teratocarcinoma Stem Cells and Their Modulation by Hormones. Connect Tissue Res. vol. 10, No. 3-4. England.

Guerriero, E., Chen, J., Sado, Y., Mohan, R. R., Wilson, S., Funderburgh, J. L., and Sundarraj, N. 2007. Loss of Alpha3(IV) Collagen Expression Associated with Corneal Keratocyte Activation. Investgative Ophthalmology & Visual Science. vol. 48, No. 2 United States.

Provenzano, P. P., Alejandro-Osorio, k, Grorud, K. W., Martinez, D. A., Vailas, A. C., Grindeland, R. E., Vanderby Jr., R. 2007. Systemic Administration of IGF-I Enhances Healing in Collagenous Extracellular Matrices: Evaluation of Loaded and Unloaded Ligaments. BMC Physiology vol. 7:2.

Saragas, S., Arffa, R., Rabin, B., Kronish, J., Miller, D., and Mayman, C. 1985. Reversal of Wound Strength Retardation by Addition of Insulin to Corticosteroid Therapy. Ann Ophthalmol 17(7):428-30.

Madibally, S. V., Solomon, V., Mitchell, R. N., Van De Water, L., Yarmush, M. L., and Toner, M. 2003. Influence of Insulin Therapy on Burn Wound Healing in Rats. Journal of Surgical Research vol. 109, pp. 92-100.

Brodovsky, S. C., Mccarty, C. A., Snibson, G., Loughnan, M., Sullivan, L., Daniell, M., and Taylor, H. R. 2000. Management of Alkali Burns an 11-Year Retrospective Review. Ophthalmology. vol. 107. pp. 1829-1835.

Ramirez, R. J., Wolf, S. E., Barrow, R. E., and Herndon, D. N. 1998. Growth Hormone Treatment in Pediatric Burns: A Safe Therapeutic Approach. Annals of Surgery vol. 228. No. 4, pp. 439-448.

Pierre, E. J., Barrow, R. E., Hawkins, H. K, Hal, K, Nguyen, T. T., Sakuri, Y., Desai, M., Wolfe, R. R., and Herndon, D. N. 1998. Effects of Insulin on Wound Healing. The Journal of Trauma, Injury, Infection and Critical Care. vol. 44(2), pp. 342-345.

* cited by examiner

COMBINATION OF INSULIN AND ASCORBATE TO ENHANCE WOUND HEALING

CROSS REFERENCE TO RELATED APPLICATIONS

This application claims priority to currently pending U.S. Provisional Patent Application 60/803,944 filed Jun. 5, 2006 and 60/823,583, filed Aug. 25, 2006 the contents of which are herein incorporated by reference.

STATEMENT OF GOVERNMENT INTEREST

This invention was made with Government support under Grant No. NEI 08104 awarded by the National Eye Institute, National Institutes of Health. The Government has certain rights in the invention.

BACKGROUND OF THE INVENTION

The corneal stroma contains keratocytes imbedded in an extracellular matrix consisting primarily of collagen types I and V and of proteoglycans that contain either chondroitin sulfate (CS) or keratan sulfate (KS) chains. Electron microscopic studies show the corneal stroma contains collagen fibrils of small, uniform diameter that are separated by small, uniformly sized spaces. The collagen fibrils in the corneal stroma are heterofibrils of collagen types I and V. Collagen type V is essential for the initiation of fibril formation and the presence of collagen V in the heterofibril has been shown to limit the fibril diameter growth. The proteoglycans are in the spaces between the fibrils in vivo (see Muller L J, Pels E, Schurmans L R, and Vrensen G F. A new three-dimensional model of the organization of proteoglycans and collagen fibrils in the human corneal stroma *Exp Eye Res.* 2004; 78:493-501; which is incorporated herein by reference) and in vitro assays that measure collagen fibril assembly have shown that these proteoglycans modulate collagen fibril formation. Collagen fibril formation in the presence of CS and KS proteoglycans purified from the cornea delayed fibril formation, decreased the rate of fibril growth and resulted in smaller collagen fibrils. The removal of the GAG side chains did not affect the activity of the proteoglycans, but reduction and alkylation abolished the activity. This indicates that the core protein of these proteoglycans modulates collagen assembly into fibrils. The major proteoglycans of the corneal stroma are decorin, lumican and keratocan. Decorin is a CS proteoglycan, whereas keratocan and lumican are KS proteoglycans. Keratocan (see iu C Y, Birk D E, Hassell J R, Kane B, and Kao W W. Keratocan-deficient mice display alterations in corneal structure *J Biol Chem.* 2003; 278:21672-21677; Meek K M, Quantock A J, Boote C, Liu C Y, and Kao W W. An X-ray scattering investigation of corneal structure in keratocan-deficient mice *Matrix Biol.* 2003; 22:467-475; which are incorporated herein by reference) and lumican (see Chakravarti S, Petroll W M, Hassell J R, et al. Corneal opacity in lumican-null mice: defects in collagen fibril structure and packing in the posterior stroma *Invest Ophthalmol Vis Sci.* 2000; 41:3365-3373; Chakravarti S, Magnuson T, Lass J H, et al. Lumican regulates collagen fibril assembly: skin fragility and corneal opacity in the absence of lumican *J Cell Biol.* 1998; 141:1277-1286; Chakravarti S. Functions of lumican and fibromodulin: lessons from knockout mice *Glycoconj J.* 2002; 19:287-293 which are incorporated herein by reference) null mice have thinner corneas, and the collagen fibrils in the stromas are larger and less organized than in the stromas of normal mice, confirming the in vitro turbidimetry analysis of collagen fibril assembly.

Three procollagen polypeptides come together to form a left-handed triple helix immediately after synthesis. Stable triple helix formation, however, can only occur if certain lysine and proline residues in the collagen molecule are hydroxylated. This post-translational hydroxylation is performed by either lysyl or prolyl hydroxylases. These enzymes are found in the lumen of the endoplasmic reticulum and require ascorbic acid as a cofactor. Ascorbate deficiency in cell culture does not affect collagen synthesis but affects fibril formation and the rate of collagen secretion. The unhydroxylated collagen molecules denature at a lower temperature and in less stringent environments than properly hydroxylated collagen fibrils. Systemic ascorbate deficiency leads to scurvy, and this deficiency affects wound healing. Scorbutic wounds are weaker than non-scorbutic wounds, prone to reopen and contain a mass of irregular, unorganized collagen fibrils.

The cornea and anterior segment of the eye contain high levels of ascorbate (see Ringvold A, Anderssen E, and Kjonniksen I. Distribution of ascorbate in the anterior bovine eye *Invest Ophthalmol Vis Sci.* 2000; 41:20-23; which is incorporated herein by reference), where it is thought to function as an antioxidant and protect the cornea from reactive oxygen species that result from UV irradiation (see Brubaker R F, Bourne W M, Bachman L A, and McLaren J W. Ascorbic acid content of human corneal epithelium *Invest Ophthalmol Vis Sci.* 2000; 41:1681-1683; which is incorporated herein by reference). The levels of ascorbate in the aqueous humor and the cornea drop following an alkali burn, resulting in the cornea becoming scorbutic. The cells in the stroma show characteristics of scorbutic tissue such as a sparse ER, suggesting that they are not very metabolically active (Pfister R R, and Paterson C A. Ascorbic acid in the treatment of alkali burns of the eye *Ophthalmology.* 1980; 87:1050-1057; which is incorporated herein by reference). Topical ascorbate has been used successfully to treat corneal alkali burns and has been proposed to do so by increasing the synthesis and secretion of properly folded collagen to replace the collagen denatured by the burn (see Pfister R R, and Paterson C A. Additional clinical and morphological observations on the favorable effect of ascorbate in experimental ocular alkali burns *Invest Ophthalmol Vis Sci.* 1977; 16:478-487; which is incorporated herein by reference). In addition, topical ascorbate has also been used post-photorefractive keratectomy (PRK) where its use decreased the late onset corneal haze (see Stojanovic A, Ringvold A, and Nitter T. Ascorbate prophylaxis for corneal haze after photorefractive keratectomy *J Refract Surg.* 2003; 19:338-343; which is incorporated herein by reference). Ascorbate concentration is highest in the epithelium, the layer that is removed prior to PRK. While the exact reason for the late onset corneal haze is not known, it is possible that removal of part of the epithelium prior to PRK results in a drop in ascorbate levels in the anterior corneal stroma and we would further speculate that this drop may reduce the secretion of properly folded collagen which could result in the haze.

Ascorbic acid has been used to study collagen synthesis in culture, but it is easily oxidized in solution and its metabolic by-products are cytotoxic in extended cell culture. A stable, non-toxic phosphate derivative of ascorbic acid (2-phospho-L-ascorbic acid) was developed and has been shown to stimulate collagen accumulation by skin fibroblasts in culture and also to enhance the secretion of type I and type III collagen peptides by rabbit keratocytes cultured in medium containing fetal bovine serum. Serum, however, contains mitogens and morphogens that cause keratocytes in culture to proliferate, acquire a fibroblastic morphology and cease keratocan expression.

SUMMARY OF INVENTION

The findings disclosed herein indicate that collagen type I assembly into fibrils is modulated by both collagen type V and the keratan sulfate proteoglycans in the stroma.

A chemically defined medium containing insulin has been previously shown to stimulate keratocyte proliferation while maintaining their dendritic morphology as well as keratocan expression (see Musselmann K, Alexandrou B, Kane B, and Hassell J R. Maintenance of the keratocyte phenotype during cell proliferation stimulated by insulin *J Biol Chem.* 2005; 280:32634-32639; which is incorporated herein by reference). In the present invention, keratocytes were cultured in this defined medium containing 2-phospho-L-ascorbic acid to determine its effects on the synthesis and accumulation of collagen and KS proteoglycans.

Collagenase isolated keratocytes were cultured with or without insulin with or without ascorbate. Collagen and glycosaminoglycan synthesis were determined by collagenase digestion of incorporated $^3$H-glycine and by chondroitinase ABC or endo-β-galactosidase digestion of incorporated $^{35}SO_4$. KSPGs were detected by Western blot. Collagen stability was determined by pepsin digestion. Ethyl-3,4-dihydroxybenzoate (EDB) was used to inhibit collagen hydroxylation.

Insulin stimulated the synthesis of collagen but did not affect the accumulation of lumican and keratocan. Insulin plus ascorbate, however, stimulated the synthesis of collagen and increased the accumulation of these proteoglycans. The accumulation of PGDS, a KSPG that does not interact with collagen, was not affected by ascorbate. Only the collagen made in the presence of ascorbate was pepsin resistant. EDB overrode the effects of ascorbate on pepsin resistance and proteoglycan accumulation.

These results indicate that the accumulation of lumican and keratocan depends, in part, upon the level of collagen synthesis and its hydroxylation. The interaction of lumican and keratocan with the stably folded triple helix provided by hydroxylation may also serve to stabilize these proteoglycans.

In a first embodiment, the invention includes a method of stimulating collagen synthesis comprising contacting a cell with a therapeutically effective amount of a compound comprising insulin and ascorbate. In a preferred embodiment the compound further comprises 2-phospho-L-ascorbic acid.

In another embodiment, the invention includes a method of stimulating wound healing, comprising contacting the wound with a therapeutically effective amount of a compound comprising insulin and ascorbate. In a preferred embodiment the compound further comprises 2-phospho-L-ascorbic acid.

In a third embodiment, the invention includes a method of inducing the secretion of collagen from a cell comprising contacting the cell with an effective amount of a compound comprising insulin and ascorbate. In a preferred embodiment the compound further comprises 2-phospho-L-ascorbic acid.

In yet another embodiment, the invention includes a method of inducing the secretion of a proteoglycan from a cell comprising contacting the cell with an effective amount of a compound comprising insulin and ascorbate. In a preferred embodiment the compound further comprises 2-phospho-L-ascorbic acid and the proteoglycan is a keratin sulfate proteoglycan selected from the group consisting of lumican and keratocan.

In another embodiment, the invention includes a method of stimulating the synthesis of pepsin resistant collagen comprising contacting a cell with an effective amount of a compound comprising ascorbate. In a preferred embodiment the compound further comprises insulin and/or 2-phospho-L-ascorbic acid.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
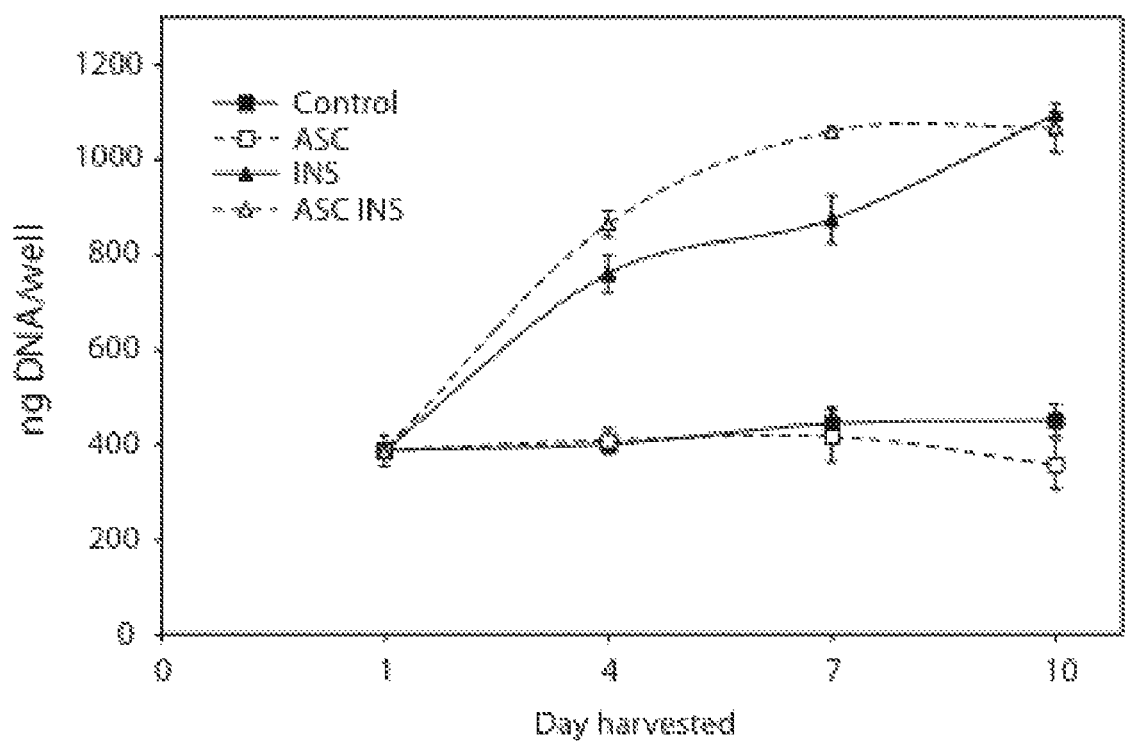
FIG. 1. Keratocyte population growth in culture using defined media. Legend: Control, filled squares solid line; ascorbate, open squares dashed line; insulin, filled triangles solid line; insulin plus ascorbate, open triangles dashed line. The addition of ascorbate to the culture medium increases initial growth rate when insulin is present in the medium but does not affect final cell density or growth in the absence of insulin. n=4

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The abbreviations used herein include:
LRR, leucine rich repeat;
DMEM/F12, Dulbecco's modified Eagle's medium and Ham's F-12 Medium, 1:1;
HRP, horse-radish peroxidase;
SDS, sodium dodecyl sulfate;
PAGE, polyacrylamide gel electrophoresis;
PDGS, prostaglandin D synthase;
PRK, photorefractive keratectomy;
ER, endoplasmic reticulum;
UV, ultraviolet light; and
ECL: electrochemiluminescence.

Ascorbate is required for the hydroxylation of collagen that is present in the corneal stroma. The keratan sulfate proteoglycans (KSPGs) lumican and keratocan, are also present and they interact with collagen and modulate its assembly into fibrils. Ascorbate was added to a defined medium containing insulin and its effects on the synthesis of collagen and KSPGs by keratocytes was determined.

Collagenase isolated keratocytes were cultured with or without insulin with or without ascorbate. Collagen and glycosaminoglycan synthesis were determined by collagenase digestion of incorporated $^3$H-glycine and by chondroitinase ABC or endo-β-galactosidase digestion of incorporated $^{35}SO_4$. KSPGs were detected by Western blot. Collagen stability was determined by pepsin digestion. Ethyl-3,4-dihydroxybenzoate (EDB) was used to inhibit collagen hydroxylation.

Insulin stimulated the synthesis of collagen but did not affect the accumulation of lumican and keratocan. Insulin plus ascorbate, however, stimulated the synthesis of collagen and increased the accumulation of these proteoglycans. The accumulation of PGDS, a KSPG that does not interact with collagen, was not affected by ascorbate. Only the collagen made in the presence of ascorbate was pepsin resistant. EDB overrode the effects of ascorbate on pepsin resistance and proteoglycan accumulation.

These results indicate that the accumulation of lumican and keratocan depends, in part, upon the level of collagen synthesis and its hydroxylation. The interaction of lumican and keratocan with the stably folded triple helix provided by hydroxylation may also serve to stabilize these proteoglycans.

These results also indicate that ascorbate alone does not increase collagen synthesis by keratocytes in culture. The addition of insulin alone, however, increased collagen synthesis 4-fold and the presence of ascorbate in medium containing insulin further increased collagen synthesis to 7-fold. The further increase in total collagen synthesis is likely due to the ascorbate-mediated hydroxylation of prolines and lysines in the collagen molecule that stabilizes the triple helix and thereby increases its secretion and resistance to degradation. Insulin has been shown to stimulate collagen type I synthesis in human lung fibroblasts at both the mRNA and protein levels, and to stimulate collagenous protein accumulation in scleroderma fibroblasts via the PKC-gamma pathway. Insulin therapy has been shown to improve wound healing of skin burns in rats. Insulin treatment has also been shown to improve the strength of healed through-and-through wounds in rabbit corneas. Since tissues derive their tensile strength from collagen, the increased strength of the corneal wounds treated with insulin may be due to increased collagen synthesis.

The addition of ascorbate to culture medium containing insulin not only stimulated collagen synthesis, but also increased keratocan and lumican accumulation 9-fold and KS synthesis 11-fold. The increase in lumican and keratocan accumulation correlates with the increased synthesis of hydroxylated collagen. Culture in insulin alone stimulated collagen synthesis, but did not affect lumican and keratocan accumulation. Although insulin stimulated collagen synthesis in the absence of ascorbate the collagen did not form stable triple helices, as shown by a greater proportion of the total collagen made accumulating with the cell layer, or pericellularly, and by the susceptibility of the collagen secreated into the medium to degradation by pepsin. When ascorbate was added to the insulin-containing medium, a higher proportion of the total collagen made was secreted into the medium and the collagens type I and V present in the medium were pepsin resistant. The effect of ascorbate on stimulating lumican and keratocan accumulation and providing resistance of collagen to pepsin digestion was abolished when ethyl-3,4-dihydroxybenzoate (EDB) was added to the culture medium. EDB is an analogue of ascorbate and competitively inhibits prolyl hydroxylase, resulting in the synthesis of underhydroxylated collagen. Taken together, these data suggest that the synthesis and accumulation of lumican and keratocan are linked to the level of collagen synthesis and to the stabilization of the collagen triple helix by hydroxylation.

The ascorbic acid mediated stimulation of keratan sulfate proteoglycan accumulated by keratocytes was limited to keratocan and lumican. Both keratocan and lumican have core proteins containing leucine rich repeats (LRR). Homology modeling of proteins with LRR to ribonuclease inhibitor show that these proteins to fold to a solenoid tertiary structure, that interacts with the collagen fibril and regulates fibril formation and diameter. PGDS is made as a keratan sulfate proteoglycan by keratocytes in culture, but it does not contain LRR and does not interact with collagen. Unlike keratocan and lumican, PGDS accumulation was not affected by insulin, ascorbate or the combination of both.

The invention shows that while insulin stimulated collagen synthesis, most of this increase was in the collagen associated with the cell layer and that when ascorbic acid was included with insulin, most of the increase was in the collagen secreted into the medium, where the proteoglycans are also secreted. Proteoglycans such as lumican and keratocan that interact with collagen may depend on the formation of a stable collagen helix for their own stability. The core protein of these proteoglycans interact with specific regions of the collagen fibril in a manner similar to the interaction of collagen with decorin. The decreased stability of the collagen triple helix that forms in the absence of ascorbate would weaken if not abolish the interaction of the core protein with the collagen. The other possibility is that the core proteins for lumican and keratocan are also hydroxylated and this stabilizes their structure and prevents proteolytic attack. It may be interesting to note that elastin, another extracellular matrix component, is also hydroxylated in the presence of ascorbate. There is, however, no evidence that the prolines or lysines in lumican and keratocan are hydroxylated and the increased synthesis of these proteoglycans in the presence of ascorbic acid is more likely due to a protective effect they receive by interaction with a stably folded collagen.

Here the inventors show that ascorbate, besides stabilizing the collagen triple helix, also increases the accumulation of lumican and keratocan proteoglycans in the medium. This data suggests that the prophylactic action of ascorbate in alkali wound treatment, and in the prevention of late onset corneal haze after PRK by the use of topical ascorbate, may be due to the effect of ascorbate on increasing the stability of the triple helix for collagen I and V which then acts to increase the stability and therefore the accumulation of the keratan sulfate proteoglycans lumican and keratocan. The increased accumulation of keratan sulfate proteoglycans, in turn, may accelerate the restoration of stromal transparency by regulating the assembly of the stably folded collagen triple helices into fibrils of the correct diameter. Insulin, which has been shown to stimulate collagen synthesis and which has been shown to improve wound healing, may further enhance wound healing if used in combination with ascorbate, particularly in humans, since they lack the ability to synthesize ascorbate.

The DNA content of the keratocyte cultures was measured over a 10-day culture period to determine if ascorbate stimulated cell accumulation. The cells cultured in DMEM/F12 or DMEM/F12 medium supplemented with ascorbate did not increase in number, but keratocytes cultured in medium supplemented with insulin increased in number over the 10-day culture period (FIG. 1). Cells cultured in insulin plus ascorbate show a moderately higher initial accumulation rate than keratocytes cultured in insulin in the absence of ascorbate and achieved the same density on day 7 as cells in insulin did on day 10. The incorporation of $^3$H-thymidine into DNA on days 1-4 and 4-7 reflected the cell accumulation rates seen for all 4 culture conditions (data not shown).

Figure 2:
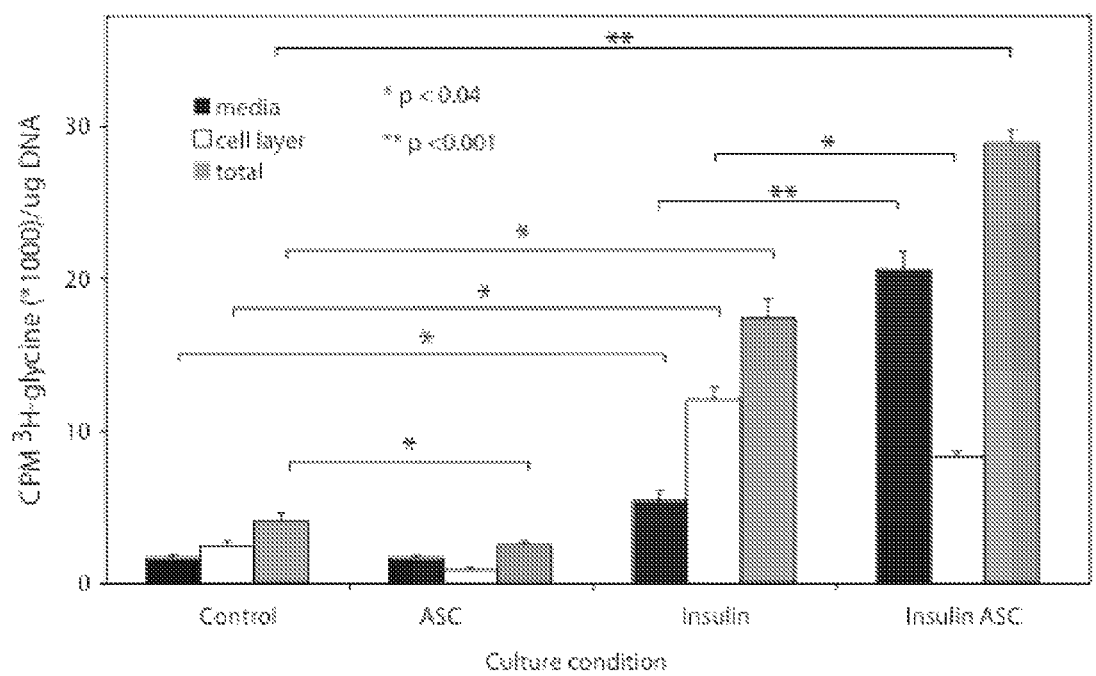
FIG. 2. Collagen synthesis and secretion in defined media. Cultures were incubated in media containing $^3$H-glycine for 72 hours. Radioactivity incorporated into collagen present in the media (black bar) and cell layer (open bar) was determined using a collagenase specific for fibrillar regions of collagen. The addition of ascorbate alone did not alter the collagen synthesis. Adding insulin to the culture medium significantly increased collagen in both the cell layer and the medium. Insulin plus ascorbate show a significant increase collagen in secreted into the medium and a significant decrease in collagen in the cell layer compared to insulin alone. n=3

The synthesis of collagen and proteoglycans was measured over 72 hours beginning on day 1 and ending on day 4, a time period during which the cell number was rapidly increasing in the cultures receiving insulin. $^3$H-glycine incorporation into collagen was determined by sensitivity to collagenase digestion (FIG. 2). Compared to control, keratocytes cultured in ascorbate synthesized 40% less collagen ($p<0.05$), and this decrease was in the collagen associated with the cell layer. Keratocytes cultured in insulin synthesized 4-fold more collagen ($p<0.01$), with increases of 5-fold in the cell layer ($p<0.02$) and 3-fold in the medium ($p<0.03$). Cells cultured in both insulin and ascorbate synthesized 7-fold ($p=0.0004$) more collagen compared to controls; a value 50% greater than insulin alone ($p=0.006$). Compared to keratocytes cultured in insulin alone, the medium of keratocytes cultured in insulin plus ascorbate contained 4-fold more collagen ($p<0.001$) but the cell layer contained 30% less collagen ($p<0.03$). Keratocytes cultured in ascorbate plus insulin synthesized 11-fold more collagen than keratocyte cultured in ascorbate alone with a 9-fold increase ($p<0.001$) in the cell layer and a 12-fold increase ($p<0.001$) in the medium. This data suggests that insulin stimulates collagen synthesis and that ascorbate increases the proportion of the collagen that is secreted into the media.

Figure 3:
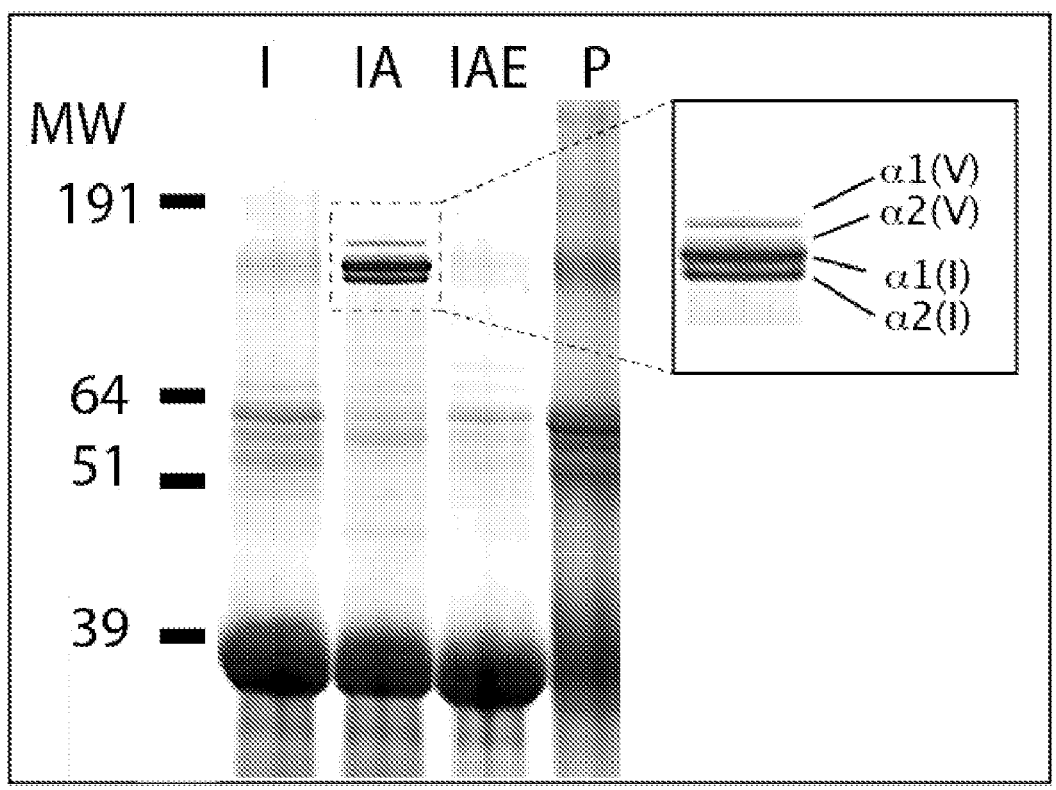
FIG. 3. SDS PAGE analysis of medium digested with pepsin. The medium of cells cultured in insulin (I), insulin plus ascorbate (IA) or insulin, ascorbate and EDB (0.4 mM) was collected, concentrated and digested with pepsin in 0.5M acetic acid. Aliquots of the digested samples and a pepsin only control (P) were separated on 10% bis-tris and stained for total protein using SafeStain™. Only the medium of cells cultured in insulin and ascorbate had pepsin resistant collagen. The IA lane is shown expanded to the right and the migration positions of the α chains for collagen I and V are labeled.

The hydroxylation of proline in the procollagen molecule is a post-translational modification required for the formation of a stable triple helix in the endoplasmic reticulum. Prolyl hydroxylases are the enzymes required for the hydroxylation of the 4-position of proline. Ethyl-3,4-dihydroxy-benzoate (EDB) is a selective inhibitor of prolyl hydroxylase. EDB is not toxic to the cells and has been previously shown to inhibit collagen deposition in a dose-dependent manner. Since most of the collagen made by keratocytes cultured in ascorbate plus insulin was in the media (FIG. 2), the collagen in the media was analyzed for stability by resistance to pepsin digestion. Keratocytes were cultured in insulin or insulin plus ascorbate-containing medium with or without 0.4 mM EDB. The medium of the cells was collected, adjusted to 0.5M acetic acid, digested with pepsin and analyzed by SDS-PAGE (FIG. 3). The medium of keratocytes cultured in insulin plus ascorbate contained pepsin-resistant collagen types I and V fibrils, demonstrated by the prominent bands for $\alpha1(I)$ and $\alpha2(I)$, as well as a clear band for $\alpha1(V)$ between the 64 and 191 kDa markers (FIG. 3, lane IA). The band for $\alpha2(V)$ partially co-migrated with $\alpha1(I)$, but can be observed as a faint band just above $\alpha1(I)$ (FIG. 3, right panel, expanded view of lane IA). These bands were absent in the medium of cells cultured in insulin alone (lane I) and in the medium of cells cultured in insulin, ascorbate and 0.4 mM EDB (lane IAE). These results show that the 2-phospho-L-ascorbic acid derivative of ascorbate acts on collagen to produce a stably folded triple helix.

Figure 4:
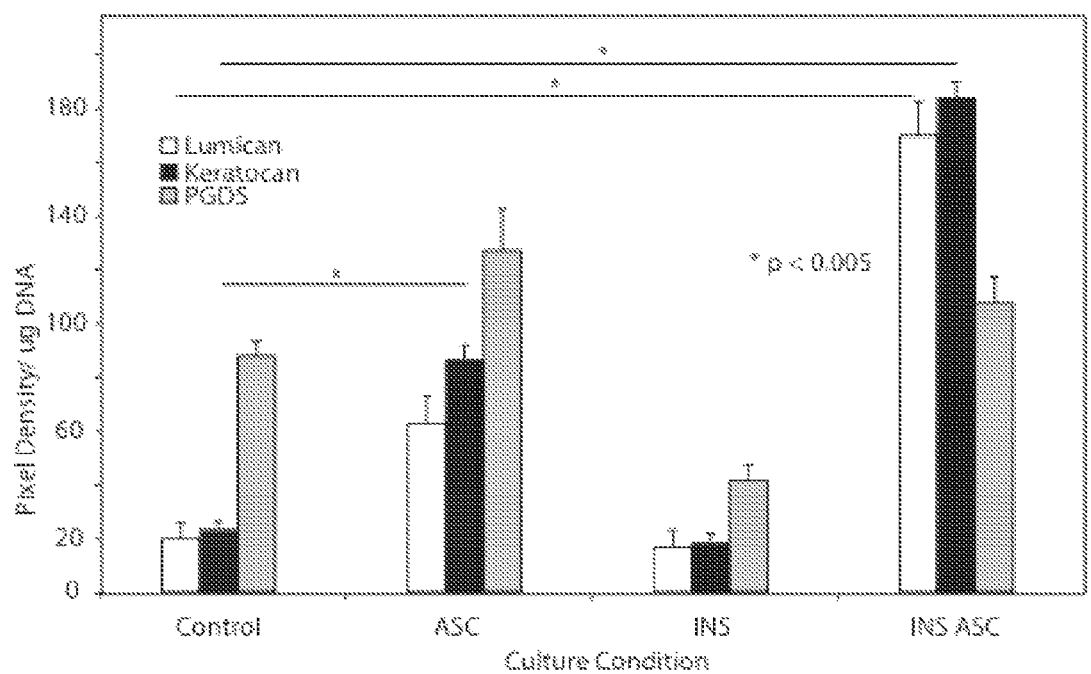
FIG. 4. Accumulation of keratan sulfate proteoglycans in the medium. Medium was collected on day 4, digested with endo-β-galactosidase, separated by SDS-PAGE, transferred to nitrocellulose and probed with antibodies to keratocan, lumican or PGDS. The Western blots using antibodies against keratocan, lumican and PGDS were scanned to determine their pixel density and the net pixel density divided by the micrograms of DNA in each culture. Bars represent the mean of 3 determinations plus S.D. Keratocan accumulation in medium containing ascorbate increased 4-fold (p<0.005) compared to control. Medium containing insulin and ascorbate contained 9-fold more keratocan and lumican (p<0.005) than control medium. The addition of ascorbate did not have an effect on PGDS levels with or without insulin. n=3

The accumulation of lumican and keratocan in the culture medium was determined by Western blot. The medium was digested with endo-β-galactosidase to remove the KS side chain before SDS-PAGE to facilitate transfer in Western blot. Antibodies to the core protein of the proteoglycan detect the core protein as a sharp band in a Western blot, and the pixel density for each band was determined (FIG. 4). Treating cells with ascorbate alone increased keratocan and lumican levels in the medium 4-fold ($p<0.005$), but insulin alone had no effect on the levels of these proteoglycans. A 9-fold increase in both lumican and keratocan was observed ($p<0.005$ for both), when cells were cultured with insulin plus ascorbate. Prostaglandin D synthase (PGDS) is also synthesized as a KSPG by keratocytes in vitro. Consequently, the inventors performed Western blots for PGDS as well and found that neither ascorbate nor insulin affected PGDS levels. Since only keratocan and lumican have been shown to interact with collagen fibrils, these results suggest that the increased accumulation of KSPGs in the medium is limited to those with core proteins that interact with collagen.

Figure 5:
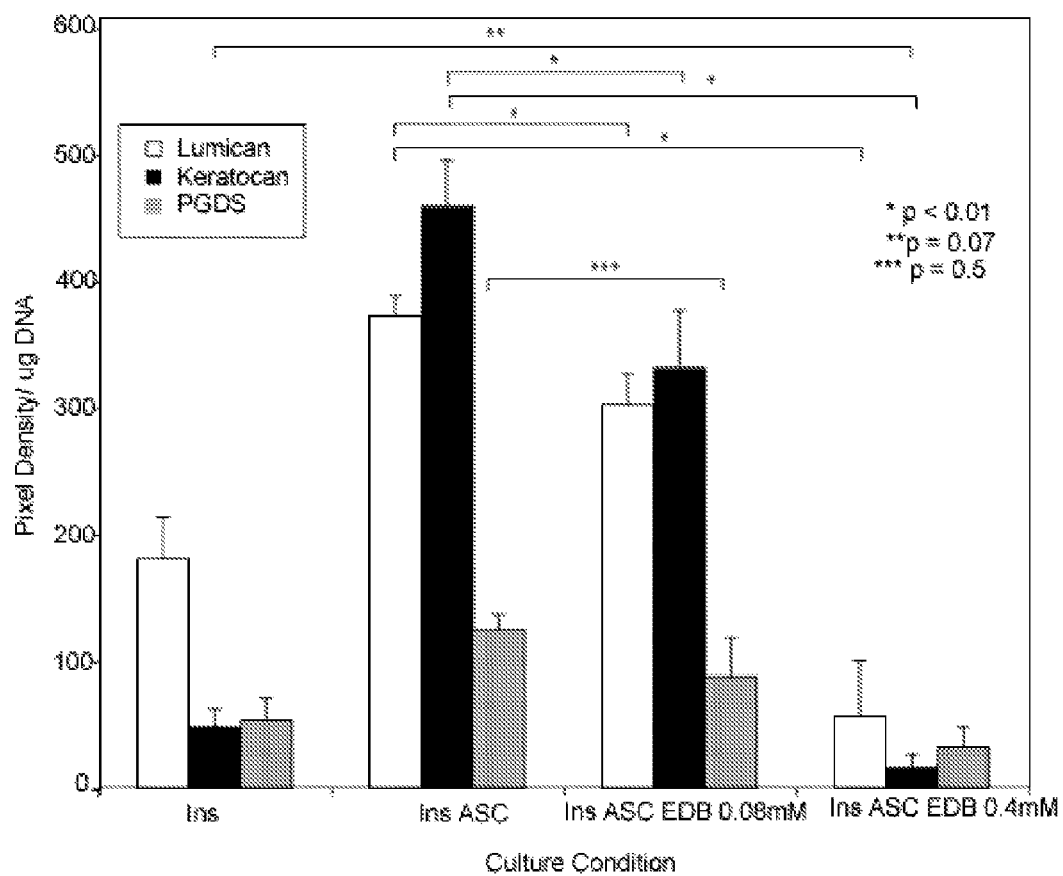
FIG. 5. Accumulation of keratan sulfate proteoglycans in culture medium of cells treated with ethyl-3,4-dihydroxybenzoate (EDB). Keratocytes were cultured in medium containing either 0.08 mM or 0.4 mM EDB in insulin containing growth medium with or without ascorbate. Samples were processed as described in FIG. 6. A dose dependent significant decrease (p<0.01) at 0.08 mM EDB was detected in both lumican and keratocan accumulation between cells cultured in insulin+ascorbate and insulin+ascorbate+EDB. At 0.4 mM, lumican and keratocan levels fell below the levels of the insulin alone control.

Having shown that the accumulation of lumican and keratocan in the medium is increased by the addition of ascorbate, the inventors then tested if the stimulatory activity of insulin plus ascorbate could be inhibited by the addition of EDB at a low and high dose (0.08 mM and 0.4 mM, respectively). As previously shown, the addition of ascorbate to medium containing insulin increased lumican and keratocan accumulation, but the presence of 0.08 mM EDB in medium containing insulin and ascorbate reduced the accumulation of both lumican and keratocan by 19 and 28% ($p<0.01$) respectively after 72 hours (FIG. 5). EDB at a high dose (0.4 mM) reduced lumican and keratocan ($p=0.07$) accumulation in the medium to levels below of those measured in insulin alone. The level of PGDS also declined but the decrease was not significant ($p=0.5$). The results of this experiment also confirm a correlation between hydroxylation and increased levels of lumican and keratocan production.

Figure 6:
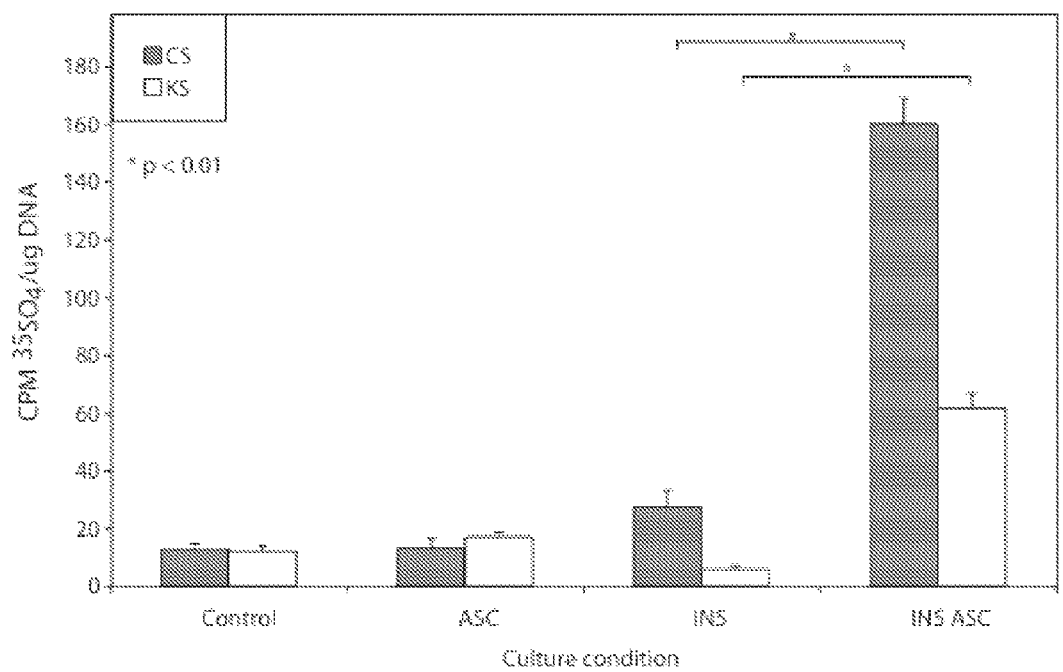
FIG. 6. Incorporation of $^{35}SO_4$ into glycosaminoglycans during 72 h in culture. Cultures were incubated in medium containing $^{35}SO_4$ for 72 hours. The culture medium was collected, sensitivity of incorporated radioactivity to chondroitinase ABC (open bars) and endo-β-galactosidase (black bars) digestion was used to determine incorporation of $^{35}SO_4$ into chondroitin and keratan sulfate, respectively. CPM was expressed per µg of DNA. Bar represent mean plus S.D. n=3.

Keratocyte cultures were radiolabeled with $^{35}SO_4$, and the amount of incorporated radiolabel in the CS and KS secreted into the media was determined by digestion with chondroitinase ABC and endo-β-galactosidase to determine if ascorbate would also increase the incorporation of $^{35}SO_4$ into KS (FIG. 6). Compared to control, the addition of ascorbate alone did not increase the incorporation of $^{35}SO_4$ into either CS or KS and insulin caused only minor changes in the incorporation of $^{35}SO_4$ into these glycosaminoglycans. Culture in insulin plus ascorbate, however, increased $^{35}SO_4$ incorporation into both CS and KS significantly ($p<0.01$), but preferentially enhanced incorporation into KS (11-fold for KS, 6-fold for CS), compared to control.

Figure 7:
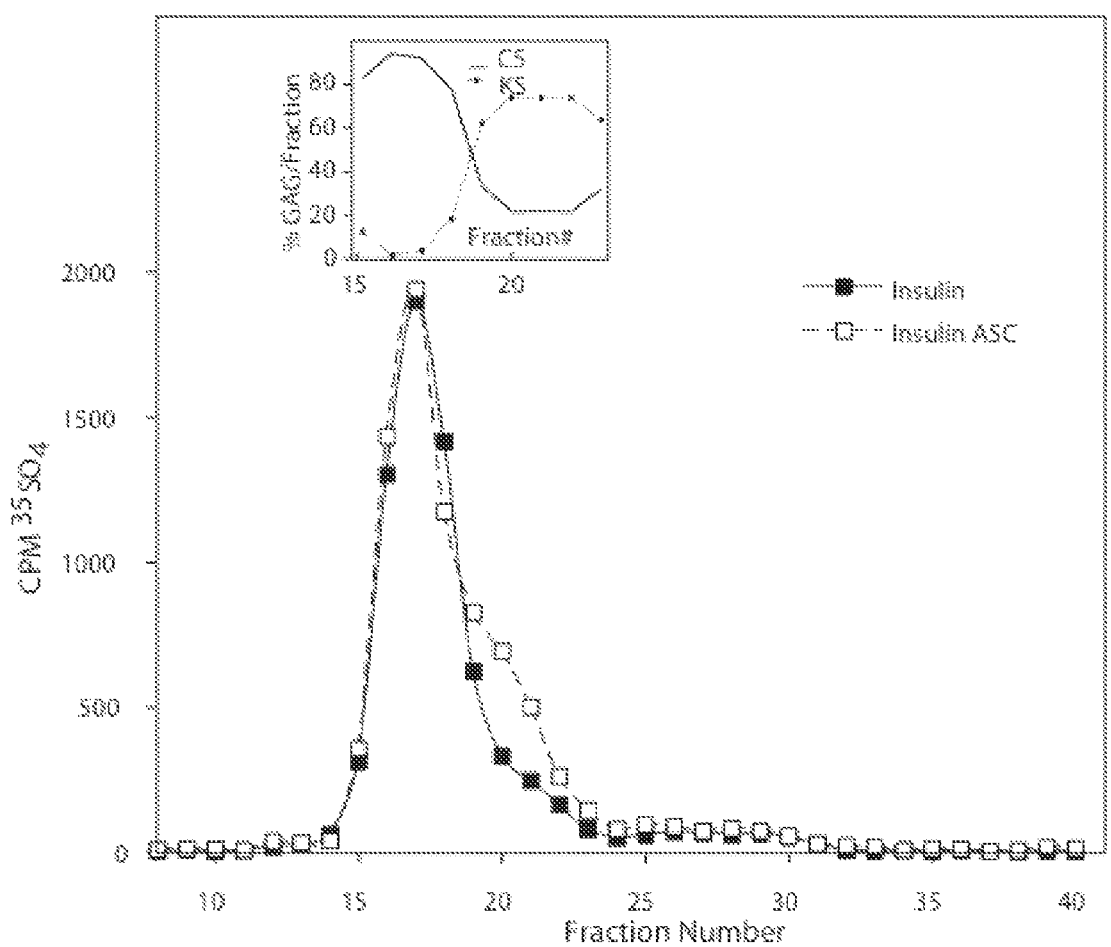
FIG. 7. Chromatography of $^{35}SO_4$ radiolabeled proteoglycans on Superose 6. Culture medium from keratocytes incubated with $^{35}SO_4$ for 72-hours was harvested and equal amounts of incorporated radioactivity was fractionated on Superose 6 to determine incorporation into intact proteoglycans. Legend: insulin: filled squares, solid line; insulin plus ascorbate: open squares, dashed line. Inlay shows percent CS/KS of fractions 15 to 23 from media of insulin plus ascorbate treated cells. Inlay legend: CS, solid line; KS, dashed line. Most of the incorporated radioactivity elutes at the position of the intact proteoglycans. Ascorbate preferentially stimulates the incorporation of $^{35}SO_4$ into KSPG.

While most of the keratan sulfate made by keratocytes in culture has been shown to be in proteoglycans, a portion accumulates as free GAG in the medium. These GAG side chains may be the result of proteolytic degradation of the core proteins. Consequently, equivalent counts of incorporated $^{35}SO_4$ present in the medium of insulin or the medium of insulin plus ascorbate treated cultures were fractionated on Superose 6 to separate intact proteoglycans from GAGs. The intact proteoglycans synthesized by keratocytes cultured in insulin or in insulin plus ascorbate eluted between fractions 15 and 23 (FIG. 7). There was, however, relatively greater incorporation in fractions 19 to 23 for keratocytes cultured in insulin plus ascorbate. Fractions 15-23 were digested with chondroitinase ABC or endo-β-galactosidase to determine the glycosaminoglycan chain composition. The inlay shows that over 80% of the incorporated counts in fractions 15-18 were released by chondroitinase ABC digestion, whereas over 60% of the incorporated counts in fractions 19-23 were released by endo-β-galactosidase digestion. This demonstrates that the KS containing proteoglycans elute primarily in fractions 19-23, and further confirms that ascorbic acid preferentially stimulates the synthesis of KS containing proteoglycans.

EXAMPLE

Chemicals—Chemicals were purchased from Sigma (St. Louis, Mo.) unless otherwise indicated. Isotopes were obtained from PerkinElmer (Boston, Mass.). Invitrogen (Carlsbad, Calif.) gels, reagents and equipment were used to separate proteins and for transfer onto nitrocellulose.

Cell Culture—Keratocytes were isolated from adult bovine corneas using two sequential collagenase digestions as previously described (see Berryhill B L, Beales M P, and Hassell J R. Production of prostaglandin D synthase as a keratan sulfate proteoglycan by cultured bovine keratocytes Invest Ophthalmol Vis Sci. 2001;42:1201-1207; which is incorporated herein by reference). Cells were plated in DMEM/F12 at high density (20,000 cells/cm$^2$) in 6-well plates (Costar, Cambridge, Mass.) and allowed to attach overnight at 37° C. in 5% $CO_2$. The medium was changed the next day (day 1) and on days 4, 7 and 10 to fresh DMEM or DMEM supplemented with insulin (10 µg/ml), with or without 1 mM 2-phospho-L-ascorbic acid (ascorbate). Ethyl-3,4-dihydroxybenzoate (EDB) was added at 0.08 mM and 0.4 mM final concentration on day 1.

DNA quantitation—Cell layers were harvested on days 1, 4, 7 and 10 to measure DNA content using Cyquant (Invitrogen, Carlsbad, Calif.). Briefly, the cell layers were rinsed with PBS, frozen, thawed and solubilized in a lysis buffer supplemented with a DNA binding dye. The DNA content was determined at 480/535 nm by measuring 4 wells in triplicate and comparing the values to a calf thymus DNA standard. The DNA content of parallel cultures was measured for experiments that utilized the cell layer.

Cell proliferation—Cultures were radiolabeled with 20 µCi $^3$H-thymidine/ml of medium for 72 hours beginning on days 1 and 4. The labeled medium was removed upon harvesting, and the cell layers washed with cold PBS. The cell layers were processed as described under DNA quantitation. Incorporation into DNA was determined as previously described.

Collagen synthesis—The incorporation of $^3$H-glycine into collagen was determined as previously described. In summary, cultures were incubated for 72 hours in medium containing 25 µCi $^3$H-glycine/ml beginning on day 1. Media was adjusted to 4M guanidine HCl and the cell layers extracted in 4M guanidine HCl. Unincorporated isotope in media and cell layers was removed by chromatography on PD10 columns equilibrated and eluted with 4M guanidine HCl (GE Healthcare, Piscataway, N.J.). Fractions containing incorporated radioactivity were pooled, dialyzed against water and 400 µl aliquots incubated with or without 2.5 Units collagenase form III (Advanced Biofactures, Lynbrook, N.Y.) in collagenase digestion medium (3 mM N-ethyl maleimide, 50 mM Tris pH 7.5, 150 mM NaCl and 5 mM CaCl2) for 3 hours at 37° C. Undigested proteins were precipitated with carrier BSA using cold 10% TCA containing 0.5% tannic acid and released incorporated counts measured by liquid scintillation. The DNA content was determined as described above.

Collagen helix stability—Medium from cells was adjusted to 0.5M acetic acid and concentrated 8-fold using Amicon Ultra spin-concentrators MWCO 10,000 (Millipore Corp., Bedford, Mass.). 50 ul of a 4 mg/ml pepsin solution (in 0.5M acetic acid) per 3 ml was added and the samples rocked overnight at 4° C. Each sample received a second 50 µl aliquot from the pepsin stock, and digestion was allowed to continue for an additional six hours at 4° C. The samples were titrated with 1N NaOH to pH 8.0 to inactivate the enzyme, dialyzed against water overnight, lyophilized, reconstituted in 1×SDS running buffer and separated on 10% bis-tris gels under reducing conditions. The gels were stained with Safestain following the manufacturers protocol.

Proteoglycan synthesis—Cultures were labeled with 50 µCi/ml of $^{35}SO_4$ for 72 hours on day 1. The medium was collected, frozen, lyophilized and reconstituted in 4M guanidine HCl. Unincorporated isotope was removed using PD10 columns. Fractions containing incorporated $^{35}SO_4$ were combined and concentrated using Amicon Ultra spin-concentrators. Incorporation into CS and KS was determined by digestion with chondroitinase ABC or endo-β-galactosidase (Seikagaku, Associates of Cape Cod, E. Falmouth, Mass.) as previously described. Aliquots containing equivalent incorporated radioactivity were fractionated using a Superose 6 12/30 HR column (GE Healthcare, Piscataway, N.J.) equilibrated and eluted with 4M guanidine HCl (0.05 NaAc, pH6.5) at 0.3 ml/min. Fractions (0.6 ml) were collected and incorporation measured by liquid scintillation counting. The levels of CS and KS in each fraction were determined as described above.

Western blot analysis—Core protein and protein levels in the media were measured by Western blot as previously described. In brief, the culture media was collected from each culture condition, concentrated by spin filtration to one tenth or one fiftieth of the original volume. The size of the aliquot needed from each sample to provide a similar signal on film by Western blot was empirically determined. The measured pixel density was then divided by the DNA content of the culture equivalent to the amount loaded and expressed as pixel density per μg DNA. Blots were probed with polyclonal antibodies to bovine keratocan or lumican (diluted 1:1000) or prostaglandin D synthase (PGDS) (1:20,000). The lumican and keratocan antibodies are peptide antibodies raised against the core protein[48]. The rabbit antiserum to bovine PGDS was a generous gift of Gary J. Killian (Penn State University). Membranes were rinsed and incubated for 1 hour in 1:10,000 horseradish peroxidase (HRP)-conjugated secondary IgG (GE Healthcare, Piscataway, N.J.). Protein bands were visualized using ECL (GE Healthcare, Piscataway, N.J.) on Kodak Bio-Max XAR X-ray film. Band density was measured using a Bio-Rad GS-710 Calibrated Imaging Densitometer (Bio-Rad, Hercules, Calif.).

Statistical Analysis—Statistical analysis was performed using Statview (SAS Institute, Cary, N.C.). Samples were analyzed using a paired t-test. Standard error was used when n>3 and standard deviation used when n=3

The compositions and/or of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19$^{th}$ ed.) describes formulations which can be used in connection with the subject invention.

Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use.

Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The administration of the compound comprising insulin, ascorbate, or any combination thereof is administered and dosed in accordance with good medical practice, taking into account the clinical condition of the individual patient, the site and method of administration, scheduling of administration, patient age, sex, body weight, and other factors known to medical practitioners.

The pharmaceutically or therapeutically "effective amount" for purposes herein is thus determined by such considerations as are known in the art.

A therapeutically effective amount of the compound comprising insulin, ascorbate, or any combination thereof is that amount necessary to provide a therapeutically effective result in vivo. The amount of the compound comprising insulin, ascorbate, or any combination thereof must be effective to achieve a response, including but not limited to increased collagen synthesis within the cell layer, increased collagen synthesis pericellularly, increased resistance of the synthesized collagen to degradation by pepsin, increased synthesis and/or secretion of lumican and/or keratocan or other indicators as are selected as appropriate measures by those skilled in the art. In accordance with the present invention, a suitable single dose size is a dose that is capable of preventing or alleviating (reducing or eliminating) a symptom or condition in a patient when administered one or more times over a suitable time period. One of skill in the art can readily determine appropriate single dose sizes for systemic administration based on the size of a mammal and the route of administration.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of increasing collagen synthesis, comprising contacting the wound with a therapeutically effective amount of a compound comprising insulin and ascorbate wherein the compound further comprises 2-phospho-L-ascorbic acid.

* * * * *